United States Patent [19]

Van Egeraat

[11] Patent Number: 5,008,910
[45] Date of Patent: Apr. 16, 1991

[54] X-RAY ANALYSIS APPARATUS COMPRISING A SAGGITALLY CURVED ANALYSIS CRYSTAL

[75] Inventor: Walterus A. L. A. Van Egeraat, Almelo, Netherlands

[73] Assignee: U.S. Philips Corporation, New York, N.Y.

[21] Appl. No.: 474,320

[22] Filed: Jan. 29, 1990

Related U.S. Application Data

[63] Continuation of Ser. No. 158,446, Feb. 22, 1988, abandoned.

[30] Foreign Application Priority Data

Feb. 27, 1987 [NL] Netherlands .......................... 8700488

[51] Int. Cl.⁵ ..................... G01T 1/36; G21K 23/201; G21K 1/06; G01N 23/223
[52] U.S. Cl. ......................................... 378/84; 378/82; 378/83; 378/85; 378/45; 378/49
[58] Field of Search ................................... 378/82-85, 378/45, 49

[56] References Cited

U.S. PATENT DOCUMENTS

| | | | |
|---|---|---|---|
| 4,091,282 | 5/1978 | Ahisovich et al. | 378/45 |
| 4,256,961 | 3/1981 | Shoji et al. | 378/85 |
| 4,261,771 | 4/1981 | Dingle et al. | 378/84 |
| 4,461,018 | 7/1984 | Ice et al. | 378/84 |
| 4,467,199 | 8/1984 | Sato | 378/49 |
| 4,780,899 | 10/1988 | Adema et al. | 378/82 |
| 4,882,780 | 11/1989 | Wittry | 378/84 |

FOREIGN PATENT DOCUMENTS

| | | | |
|---|---|---|---|
| 1180719 | 6/1959 | France | 378/84 |
| 0066156 | 4/1986 | Japan | 378/83 |

OTHER PUBLICATIONS

Chen, C. T., Concept and Design Procedure for Cylindrical Element Monochromators for Synchrotron Radiation, Nuclear Instrument, and Methods in Physics Research, A256 (1987), pp. 595–604.

Yaakohi et al., Focusing X-Ray Spectrograph for Laser Fusion Experiments, Rev. Sci. Instrum., 50(12), Dec. 1979, pp. 1609–1611.

Primary Examiner—Edward P. Westin
Assistant Examiner—Don Wong
Attorney, Agent, or Firm—Paul R. Miller

[57] ABSTRACT

An X-ray analysis apparatus comprises an analysis crystal which is cylindrically curved in the saggital direction. As a result, a beam diffracted by the crystal is collimated in that direction, i.e. the plane of incidence of the X-ray beam, so that a substantial gain regarding radiation yield is obtained without loss of resolution.

3 Claims, 1 Drawing Sheet

X-RAY ANALYSIS APPARATUS COMPRISING A SAGGITALLY CURVED ANALYSIS CRYSTAL

This new continuation application is a continuation of previous application Ser. No. 07/158,446, filed Feb. 22, 1988, and all benefits for such earlier application are hereby claimed for this new continuation application.

The invention relates to an X-ray analysis apparatus, comprising an X-ray source, an X-ray detector and an analysis crystal, and also relates to an analysis crystal for such an X-ray analysis apparatus.

An apparatus of this kind is known from German Patent No. DE 35 24 379. An X-ray spectrometer described therein utilizes an analysis crystal for dividing radiation originating from a specimen to be examined into a spatial wavelength spectrum. Radiation emerging from the crystal is intercepted by a detector. In the case of an ideal crystal, a fixed direction with respect to the normal to the crystal exists for the diffracted beam for each wavelength. Among others crystal defects, that is to say disturbances of in the regularity of the crystal surfaces, result in errors in the diffraction direction (meridional) but also in lateral (saggital) dispersion of the radiation.

In an efficient measurement set-up, it is desirable that a specimen is also irradiated across the entire width in a direction transversely of the diffraction direction. Because of the dispersion already present in the incident beam and the enlargement thereof by the specimen, the collimation of the beam incident on the crystal is already substantially reduced. At that area, viewed in the lateral direction, the beam customarily has a comparatively large dimension, so that a comparatively large radiation dispersion also occurs in that direction. After diffraction on the crystal, therefore, a comparatively wide beam is incident on the entrance diaphragm of an entrance window of the detector. Because the dimensions of the detector entrance surface are limited, a substantial part of the beam will not be detected.

It is the object of the invention to provide an apparatus having a higher radiation efficiency; to achieve this, an X-ray analysis apparatus of the kind set forth in accordance with the invention is characterized in that the analysis crystal is curved so as to be substantially circular-cylindrical in the saggital direction, the radius of curvature being adapted to the geometry of parts of the apparatus.

When the crystal is curved in the saggital direction with a radius of curvature adapted to the beam path in the apparatus, a substantial gain is achieved as regards the useful radiation yield. The saggital direction is to be understood to mean herein the direction transversely of a plane through the incident main beam the normal to the crystal center and the diffracted main beam. The radius of curvature R of the crystal notably depends on the angle of incidence $\theta$, with a distance a between the front side of a primary collimator and the crystal, equal to $a/\sin \theta$.

The crystal in a preferred embodiment is curved so as to be circular-cylindrical, this can be realized in a simple and well-defined manner. The center of curvature of the crystal notably coincides with an entrance side of a primary collimator arranged between an X-ray source and the crystal, notably a soller slit.

Some preferred embodiments in accordance with the invention will be described in detail hereinafter with reference to the drawing, wherein.

Figures 1, 2:
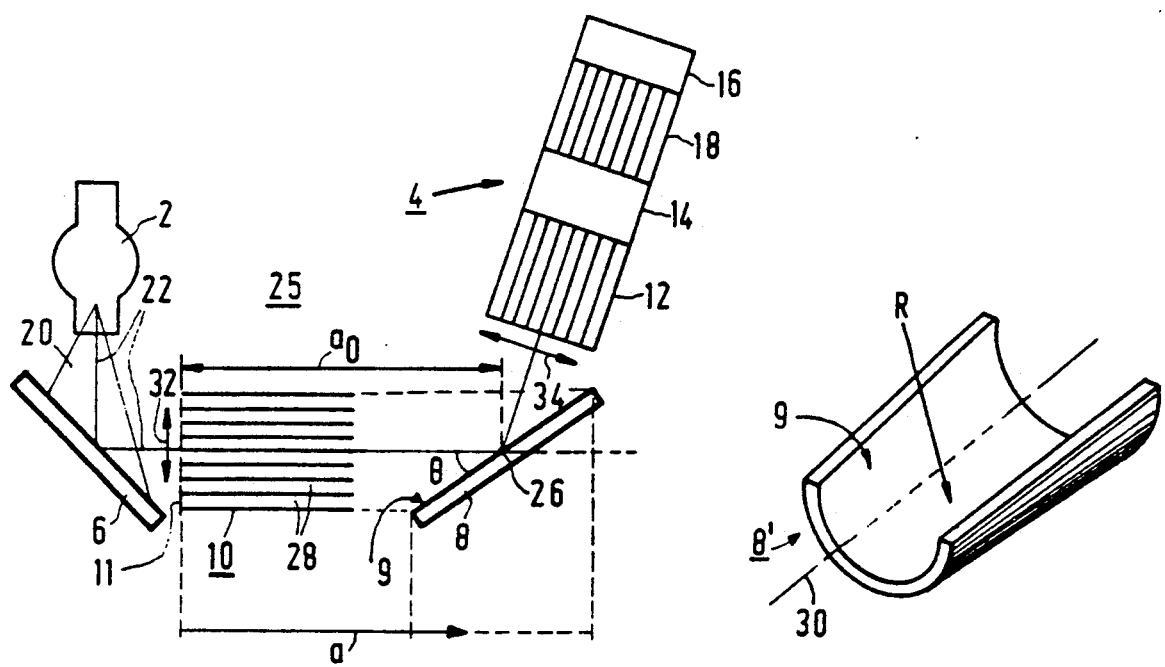
FIG. 1 shows an x-ray apparatus according to the invention.
FIG. 2 shows an analysis crystal according to the invention.

FIG. 1 of the drawing shows an X-ray spectrometer which includes an X-ray source 2, an X-ray detector 4, a specimen 6, an analysis crystal 8 having a detection surface 9, a radiation entrance diaphragm 10 with an entrance face 11, and a radiation exit diaphragm or detector entrance diaphragm 12. The diaphragms are constructed as soller slits and the detector is composed of a flowcounter 14 and a scintillation detector 16, a further collimator 18 being arranged between the two detector elements. All the elements are arranged in a plane which coincides with the plane of drawing. An X-ray beam 20 emerging from the source is incident on the detector 4 via the specimen 6, the entrance collimator 10, the analysis crystal 8 and the exit collimator 12. A main ray 22 of the beam 20 remains within an entrance plane 25 of the beam. This entrance plane also coincides with the plane of drawing. In the case of such an arrangement and beam path, the main ray 22 of the X-ray beam strikes the crystal at a point 26 and a plane through said main ray, transversely of the plane of drawing, so parallel to the soller slit plates 28, intersects the crystal along an axis 30 which is shown in FIG. 2 and a perspective view of the crystal 8' for the sake of clarity. In a dispersion direction which is denoted by an arrow 32 the incident beam is collimated by the soller slit and the same takes place for the diffracted beam for which the diffraction direction is indicated by an arrow 34. In the saggital direction transversely of the diffraction direction, also in this case transversely of the plane of the drawing, no collimation occurs, ignoring the lateral boundaries of the collimators. The use of a further soller slit comprising plates for this direction would reduce the intensity of the X-ray beam to an unacceptably low level. For this direction a substantial gain regarding radiation yield is obtained by bending the crystal so as to be cylindrical as shown in FIG. 2. A radius of curvature R then preferably equals the distance a between an entrance plane of the soller slit or of an otherwise shaped entrance diaphragm or entrance slit and the point of incidence 26 which is then divided by $\sin \theta$. The radius of curvature R, however, need not necessarily be exactly equal to that distance but can be adapted to specific requirements or dimensions and to the construction of the apparatus. For example, the radius of curvature can be optimized for minimum angular errors for the incident beam, viewed across the crystal dimension in the saggital direction. Notably for the long wave spectral range, i.e. for small values of $\theta$, such a crystal shape results in a substantial gain as regards radiation efficiency.

What is claimed is:

1. An x-ray analysis apparatus comprising in order an x-ray source passing an x-ray beam; a sample reflecting said x-ray beam; at least a primary soller slit collimator collimating said x-ray beam from said sample; a curved analysis crystal receiving said x-ray beam from said collimator, said analysis crystal being substantially circular-cylindrical in a saggital direction transverse to a plane extending through an incident x-ray beam to said analysis crystal and a normal to said analysis crystal, and said analysis crystal producing a diffracted x-ray beam, said circular-cylindrical analysis crystal having a radius of curvature R substantially equivalent to a distance between an entrance side of said primary soller slit collimator and a point of incidence of said incident x-ray beam on a surface of said analysis crystal divided by sin $\theta$, where $\theta$ is an angle of incidence of said incident x-ray beam on said analysis crystal; and an x-ray detector receiving said diffracted x-ray beam and having at least one further collimator.

2. An x-ray analysis apparatus according to claim 1, wherein said analysis crystal is disposed upon a carrier, and wherein said analysis crystal has a circular-cylindrical curved and exposed diffraction face.

3. An x-ray analysis apparatus according to claim 1, wherein said x-ray detector includes in the direction of said diffracted x-ray beam a radiation entrance diaphragm including said further collimator, a flowcounter, another collimator, and a scintillation detector.

* * * * *